United States Patent
Stibich et al.

(10) Patent No.: US 9,504,345 B2
(45) Date of Patent: Nov. 29, 2016

(54) CONTAINMENT CURTAINS AS WELL AS SYSTEMS AND APPARATUSES INCLUDING SAME

(71) Applicant: Xenex Disinfection Services LLC., San Antonio, TX (US)

(72) Inventors: Mark A. Stibich, Santa Fe, NM (US); Morris Miller, Austin, TX (US); Ricardo Flores-Clar, Jr., San Antonio, TX (US); Sarah E. Simmons, San Antonio, TX (US); Rachael A. Sparks, San Antonio, TX (US); Paul P. Froutan, Katy, TX (US); Julie A. Stachowiak, Santa Fe, NM (US); Daniel F. S. English, Holyoke, MA (US)

(73) Assignee: Xenex Disinfection Services, LLC., San Antonio, TX (US)

( * ) Notice: Subject to any disclaimer, the term of this patent is extended or adjusted under 35 U.S.C. 154(b) by 0 days.

(21) Appl. No.: 15/092,779

(22) Filed: Apr. 7, 2016

(65) Prior Publication Data

US 2016/0249760 A1    Sep. 1, 2016

Related U.S. Application Data

(63) Continuation of application No. PCT/US2014/059698, filed on Oct. 8, 2014.

(60) Provisional application No. 61/888,354, filed on Oct. 8, 2013.

(51) Int. Cl.
*A47H 13/00* (2006.01)
*A61G 12/00* (2006.01)
(Continued)

(52) U.S. Cl.
CPC ............... *A47H 13/00* (2013.01); *A47H 1/19* (2013.01); *A47H 21/00* (2013.01); *A47H 23/08* (2013.01); *A61G 12/00* (2013.01); *A47H 2201/01* (2013.01); *A47H 2201/02* (2013.01)

(58) Field of Classification Search
CPC ................................. A47H 13/00; A47H 1/00
See application file for complete search history.

(56) References Cited

U.S. PATENT DOCUMENTS

| | | | | |
|---|---|---|---|---|
| 3,321,003 A | * | 5/1967 | Boerner | A47H 23/04 160/237 |
| 4,333,187 A | * | 6/1982 | Schuler | A47K 3/38 160/330 |

(Continued)

FOREIGN PATENT DOCUMENTS

| | | |
|---|---|---|
| CN | 201558350 | 8/2010 |
| EP | 0252571 | 7/1987 |

(Continued)

OTHER PUBLICATIONS

Notification of Transmittal of the International Preliminary Report, PCT/US2014/059698, Jan. 29, 2016, 25 pgs.

(Continued)

*Primary Examiner* — David Purol
(74) *Attorney, Agent, or Firm* — Egan Peterman Enders Huston

(57) ABSTRACT

Curtains are provided which have fastener/s and, in some cases, strut/s arranged along a screen. The strut/s extend to elevation/s below and/or above the fastener/s. An upper strut may have a lower degree of stiffness than a lower strut. In some cases, the fastener/s are arranged at least 20 inches from the screen's upper edge. Systems are described which include a disinfection apparatus and any of such curtains. Other systems include any of such curtains attached to an edge of a room divider. Easily assembled and disassembled room dividers are described which include cord/s and/or pole/s, installed or portable device/s for supporting the cords/poles, and fasteners for attaching a curtain to the cords/poles. A disinfection apparatus is described which includes a shield extending to an elevation at least two feet above a germicidal light source and borders at least one third of a continuous region surrounding the germicidal light source.

28 Claims, 9 Drawing Sheets

(51) Int. Cl.
*A47H 21/00* (2006.01)
*A47H 23/08* (2006.01)
*A47H 1/19* (2006.01)

(56) References Cited

U.S. PATENT DOCUMENTS

| | | | |
|---|---|---|---|
| 5,217,057 A * | 6/1993 | Hubbard | A47H 5/00 160/123 |
| 5,680,893 A | 10/1997 | Neer | |
| 6,474,396 B1 * | 11/2002 | Toder | A47H 13/04 160/237 |
| 7,523,778 B2 * | 4/2009 | Roberts | A47H 23/08 160/237 |
| 2006/0252326 A1 | 11/2006 | Mishler | |
| 2009/0191100 A1 | 7/2009 | Deal | |
| 2009/0283120 A1 | 11/2009 | Varga et al. | |
| 2012/0313532 A1 | 12/2012 | Stibich et al. | |

FOREIGN PATENT DOCUMENTS

| | | |
|---|---|---|
| GB | 637085 | 5/1950 |
| WO | 2007076359 | 7/2007 |

OTHER PUBLICATIONS

International Search Report and Written Opinion, PCT/US2014/059698, May 15, 2015, 17 pgs.
Written Opinion of the International Preliminary Examining Authority, PCT/US2014/059698, Sep. 28, 2015, 9 pgs.

* cited by examiner

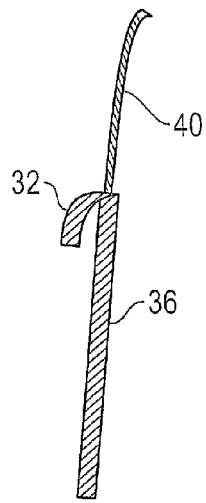
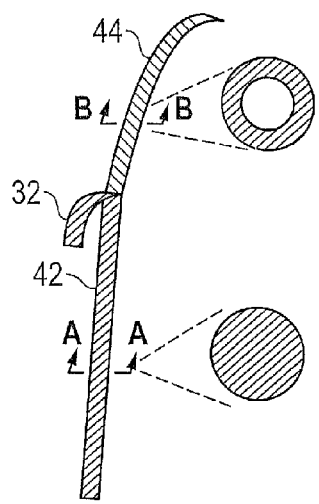
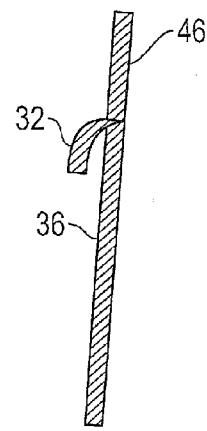
FIG. 2A    FIG. 2B    FIG. 2C
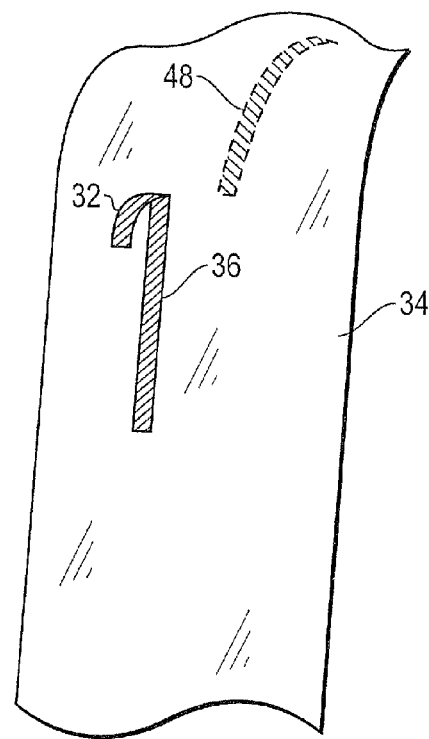
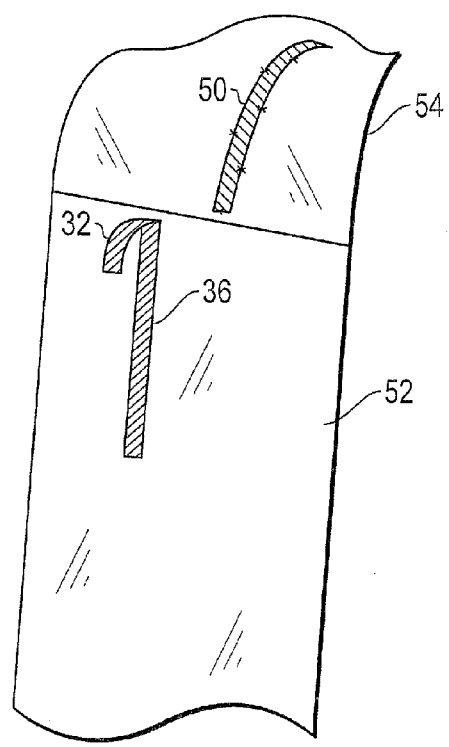
FIG. 2D    FIG. 2E

CONTAINMENT CURTAINS AS WELL AS SYSTEMS AND APPARATUSES INCLUDING SAME

PRIORITY CLAIM

This application is a continuation of pending International Patent Application No. PCT/US2014/059698 filed Oct. 8, 2014, which designates the United States and claims priority to U.S. Provisional Patent Application No. 61/888,354, filed Oct. 8, 2013.

BACKGROUND OF THE INVENTION

1. Field of the Invention

This invention generally relates to containment curtains and, more specifically but not limited to, containment curtains for rooms which typically have multiple occupancy as well as systems and apparatuses including such containment curtains.

2. Description of the Related Art

The following descriptions and examples are not admitted to be prior art by virtue of their inclusion within this section.

Area/room disinfection is becoming increasingly important as pathogenic microorganisms have been shown to cause infections when present in occupied rooms or areas. This is especially important as antimicrobial resistant organisms are becoming more prevalent and increasingly difficult to treat. Examples of area/room disinfection applications are those used in hospitals and those used in agricultural operations, such as for breeding and/or farming animals. In general, the objective of area/room disinfection is to reduce the number of pathogenic microorganisms in an area/room to a level which is much less harmful to human health. In order to limit or prevent exposure of germicides and/or distractions to occupants of a room or area, area/room disinfection is typically performed by trained cleaning personnel or by an automated device after a room has been vacated by the previous occupants. Complete evacuation of some areas/rooms, however, is sometimes difficult to attain due to the use of the area/room. For example, multiple occupancy rooms, such as but not limited to multiple occupancy patient rooms in hospitals, and/or relatively large high traffic areas with ambiguous boundaries, such as but not limited to nurses' stations in hospitals, can sometimes be difficult to evacuate for disinfection of the entire area/room.

In some embodiments, portions of multiple occupancy rooms and/or relatively large high traffic areas can be sectioned off using a room divider to establish a vacated area for area/room disinfection procedures. For example, a cubicle curtain in a multiple occupancy patient room may be drawn around a single patient bed after the patient has left or a floor based paneled screen may be used to section off a portion of an area/room. In many of such cases, however, the room divider does not provide a barricade from floor to ceiling and, in some embodiments, the body portion of the room divider may be partially transparent and/or have open areas. Consequently, in many of such cases, persons occupying an area/room outside a region sectioned off by the room divider are undesirably exposed to the germicide and/or distractions of a disinfection process performed in the sectioned off region. For some disinfection processes, such as but not limited to those which utilize ultraviolet electromagnetic radiation subtype C (UVC) light, human exposure to the germicide is prohibited or needs to be minimized to undetectable levels and, thus, such disinfection processes typically cannot be used for regions of an area/room sectioned off by a room divider which is transparent and/or does not completely barricade a region.

Accordingly, it would be beneficial to develop screens which serve to better barricade regions of a room, particularly in conjunction with but not limited to existing room dividers. In addition, it would be advantageous to develop systems and apparatuses including such screens. It would be further beneficial to configure the screens, systems, and apparatuses to be easily set up, handled and stored.

SUMMARY OF THE INVENTION

The following description of various embodiments of apparatuses is not to be construed in any way as limiting the subject matter of the appended claims.

Embodiments of curtains include a screen configured to attenuate a majority amount of the visible light spectrum and/or a majority amount of the UVC light spectrum and one or more fasteners disposed along the screen at least 20 inches from an upper edge of the screen, wherein the one or more fasteners are configured for attaching the curtain to an object.

Other embodiments of curtains include a screen, one or more fasteners disposed along the screen, and one or more struts coupled to the one or more fasteners, wherein the one or more struts extend to an elevation at least 24 inches below the one or more fasteners.

Yet other embodiments of curtains include a pliable screen and a fastener disposed along the pliable screen, wherein the fastener is configured for attaching the curtain to an object. Such curtains further include a lower strut coupled to the fastener and extending to an elevation below the fastener as well as an upper strut coupled to the pliable screen, wherein the upper strut extends to an elevation above the fastener, and wherein the upper strut comprises a lower degree of stiffness than the lower strut.

Embodiments of systems include a disinfection apparatus comprising one or more germicidal light sources and a curtain of any of the aforementioned embodiments.

Other embodiments of systems include a room divider having an edge disposed at least four feet from a floor of a room and an auxiliary curtain of any of the aforementioned embodiments attached to the edge.

Embodiments of room dividers include one or more cords and a plurality of portable devices for supporting the one or more cords, wherein each of the plurality of portable devices has one of the cords attached thereto or is configured to receive attachment of one of the cords. The room dividers further include a means for removably securing each of the plurality of portable devices in different locations in a room, a curtain, a plurality of fasteners for attaching the curtain to one of the one or more cords suspended between two of the portable devices, and a means for affecting mobility of the one or more cords, the plurality of portable devices, the curtain, and the plurality of fasteners together.

Other embodiments of room dividers include one or more cords or poles and one or more devices for supporting the one or more cords or poles, wherein each of the one or more devices has one of the cords or poles attached thereto or is configured to receive attachment of one of the cords or poles. The room dividers further include a curtain of any of the aforementioned embodiments.

Embodiments of a disinfection apparatus includes a germicidal light source arranged within the apparatus to emit light into an ambient of a room in which the apparatus is arranged, a support structure supporting a base of the germicidal light source, and a shield attached to the support structure. The shield extends to a first elevation at least two feet above the germicidal light source and borders at least one third of a continuous region surrounding the germicidal light source. In addition, the shield is configured to block a majority amount of the visible light spectrum and/or a majority amount of the ultraviolet electromagnetic radiation subtype C light spectrum.

BRIEF DESCRIPTION OF THE DRAWINGS

Other objects and advantages of the invention will become apparent upon reading the following detailed description and upon reference to the accompanying drawings in which:

FIGS. 2a-2c illustrate alternative configurations for the composite fastener/strut components illustrated in FIG. 1;

FIG. 2d illustrates a curtain having an upper strut spaced apart from a lower strut and fastener of the curtain;

FIGS. 2e and 2f illustrate curtains having an alternative placement of upper struts and alternative configurations of screens relative to FIG. 1;

Figure 1:
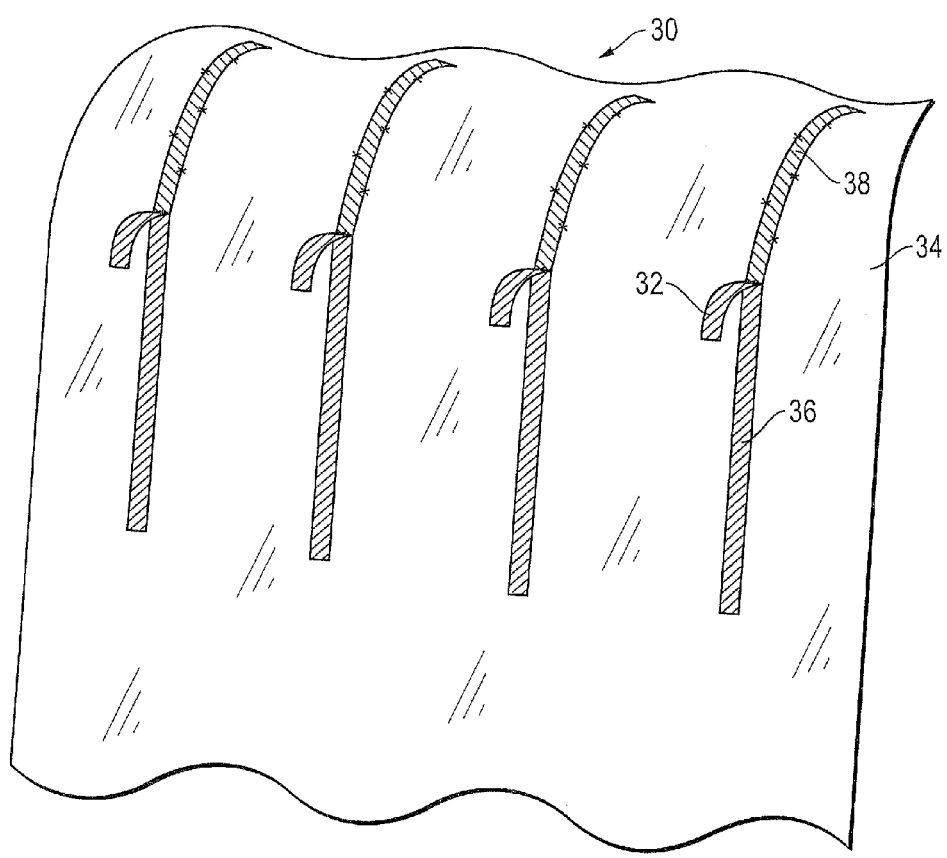
FIG. 1 illustrates a curtain having fasteners affixed to a sheet of material and struts of different materials extending above and below the fasteners.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 2F:
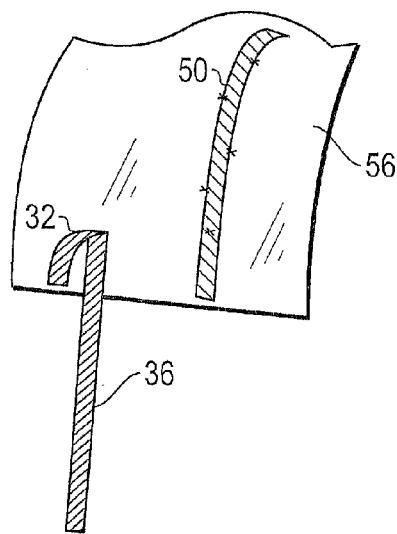
Figure 2G:
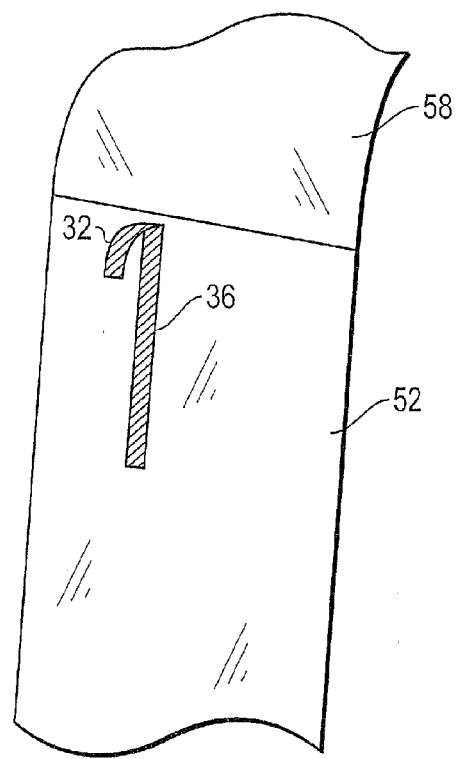
FIGS. 2g and 2h illustrate curtains absent upper struts and having alternative configurations of screens relative to FIG. 1.
Figure 2H:
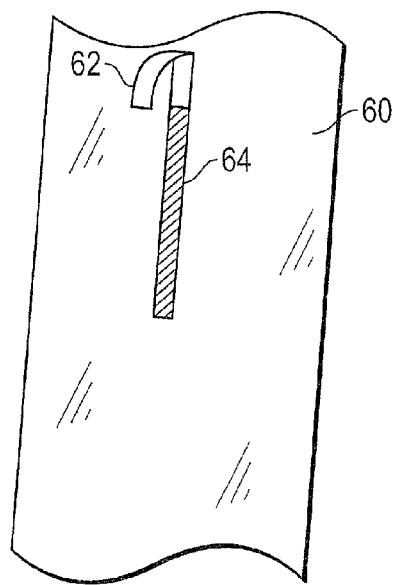
Figure 2I:
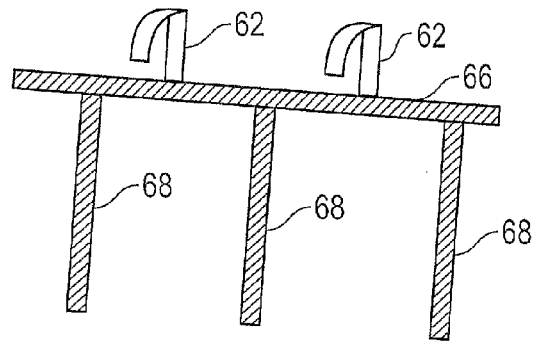
FIG. 2i illustrates an alternative configuration for the composite fastener/strut components illustrated in FIG. 1.
Figure 2J:
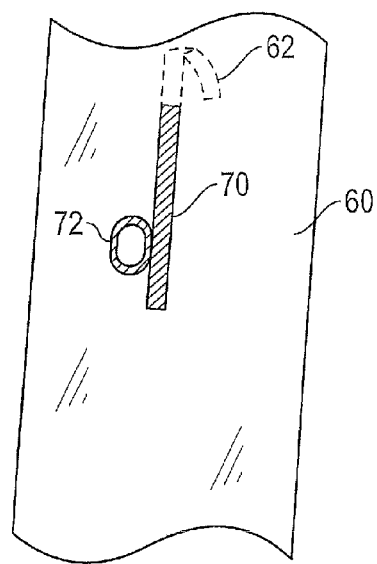
FIG. 2j illustrates a curtain having a lower strut with a handle and a fastener disposed on an opposite side of a screen than the handle.
Figure 3A:
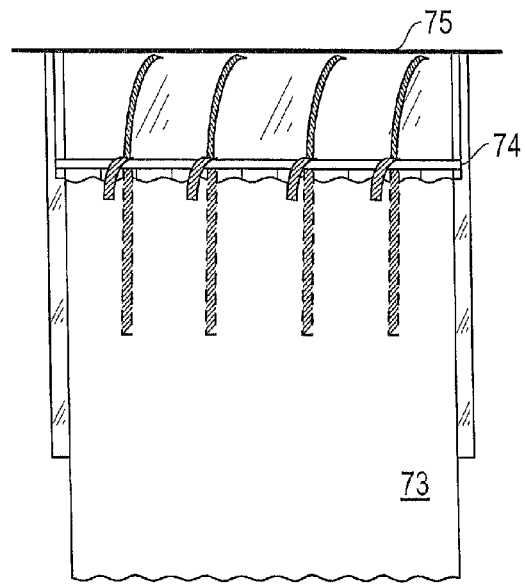
FIGS. 3a-3c illustrate examples of curtains having fasteners and lower struts attached to various room dividers.
Figure 3B:
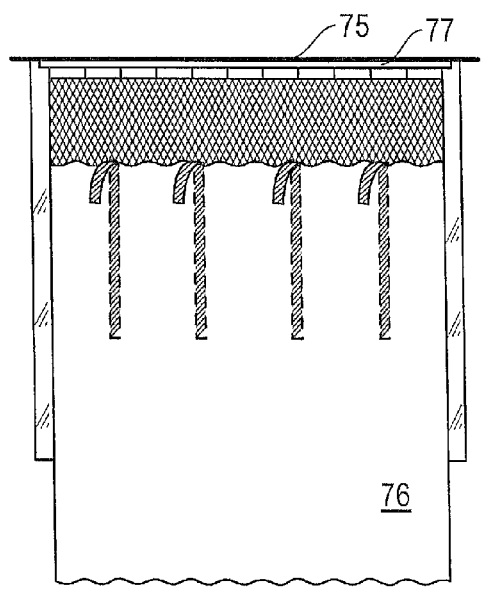
Figure 3C:
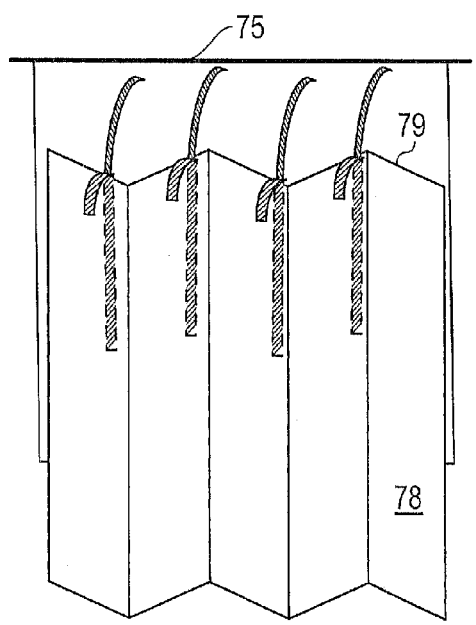
Figure 4:
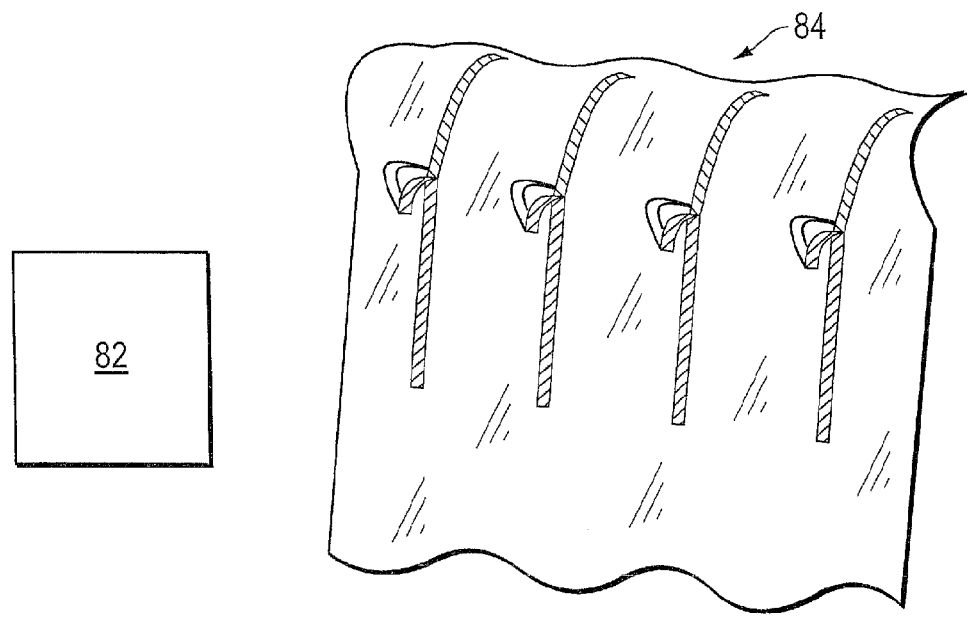
FIG. 4 illustrates a system including a disinfection apparatus and a curtain with fasteners and struts.

Turning to the drawings, examples of curtains as well as different configurations of components comprising such curtains are shown in FIGS. 1-2j. Furthermore, FIGS. 3a-3c illustrate example uses of such curtains and FIGS. 4-5c depict example systems and uses of curtains with disinfection sources. It is noted that although the curtains described herein are emphasized for use in conjunction existing room dividers, particularly room dividers commonly used in patient settings (such as cubicle curtains), the use of the curtains described herein is not necessarily so limited. In particular, the curtains described herein may be used in any environment and for any use in which it may be desirable to conceal an area, block light, decorate an area, divide a room and/or increase privacy. Moreover, the curtains described herein need not be hung on a room divider, but rather may be hung on any structure. Furthermore, although the curtains described herein are emphasized for use in conjunction with disinfection apparatuses, particularly those which include germicidal lamps, the use of the curtains described herein is not necessarily so limited. In particular, the curtains described herein may be used without employing a disinfection apparatus. As will be set forth in more detail below, the curtains and systems described herein are not limited to the depictions in the drawings. Furthermore, it is noted that the drawings are not necessarily drawn to scale in that particular features may be drawn to a larger scale than other features to emphasize their characteristics.

Turning to FIG. 1, curtain 30 is shown having fasteners 32 affixed to one side of screen 34 and disposed between lower struts 36 and upper struts 38. In general, fasteners 32 may include any means by which to attach screen 34 to an object. Although hooks are emphasized herein, other types of fasteners may be considered for fasteners 32, including but not limited to clips, ties, snaps, pins, clasps, buckles, magnets, and loops engageable with a hook (e.g., the eye component of a hook and eye complementary fastener). Furthermore, screen 34 and fasteners 32 may include any combination of any materials and any fasteners which yield curtain 30 to be hung. More specifically, fastener/s and material/s may be selected such that the fastener/s are sufficient to couple and hold the material/s to an object, taking into consideration the weight and configuration of the material. In any case, curtain 30 may include any number of fasteners, including a single fastener or a plurality of fasteners greater or less than the four fasteners depicted in the example of FIG. 1.

It is noted that the reference of curtain 30 as a piece of material to be hung refers to the curtain being capable for suspension, but does not infer the curtain does not come into contact with other objects or surfaces. In particular, the curtains described herein may, in some embodiments, be configured to touch the floor, the ceiling or other objects or surfaces of a room in which they are hung. The term room as used herein refers to a space in which an adult human being of average size may comfortably occupy for at least a period of time to eat, sleep, work, lounge, partake in an activity, or complete a task therein. Examples of rooms include but are not limited to single patient rooms, multiple occupancy patient rooms, bathrooms, walk-in closets, hallways, bedrooms, offices, operating rooms, patient examination rooms, waiting and/or lounging areas and nursing stations. In some cases, rooms may be bounded and include a door for entering and exiting the room. In other cases, a room may be an area with indeterminate boundaries. In view of the latter, it is noted that the room dividers described herein may be alternatively referred to as area dividers.

As shown in FIG. 1, fasteners 32 may, in some cases, be disposed on the same side of screen 34 as lower struts 36 and upper struts 38. In other embodiments, however, fasteners 32 may be disposed on the other side of screen 34 (i.e., the side of screen 34 opposing the side on which lower struts 36 and upper struts 38 are disposed). In yet other cases, lower struts 36 and upper struts 38 may be disposed on opposing sides of screen and fasteners 32 may be affixed to either side of screen 34. As an alternative to any of such cases, fasteners 32 may, in some embodiments, be disposed to both sides of screen 34. In some cases, any or all of lower struts 36 and upper struts 38 may be disposed within screen 34. Further yet, regardless of whether lower struts 36 and/or upper struts are disposed exterior or interior to screen 34, one or more of fasteners 32 may be disposed within interior portions of screen 34 and then extend out to one or both sides of screen 34.

In some cases, it may be advantageous to have fasteners 32 disposed on an opposing side of screen 34 as lower struts 36. In particular, such a configuration may allow an individual grasping lower struts 36 on one side of curtain 30 to more easily mount the curtain in a forward motion away from the individual's body or at least make mounting the curtain in such a manner more intuitive. It is conceivable, however, that mounting curtain 30 in a forward motion away from a individual's body may be achieved by an individual grasping screen 34 around lower struts 36 when lower struts 36 are disposed interior to screen 34 or are disposed on the same side of screen 34 as fasteners 32. In yet other cases, curtain 30 may be mounted in a backward motion toward the body of the individual mounting the curtain. In such embodiments, it may be advantageous for fasteners 32 to be disposed on the same side of screen 34 as lower struts 36, although lower struts 36 could alternatively be disposed interior to screen 34 or on the other side of screen 34.

In any case, fasteners 32 may be disposed at or near the upper edge of screen 34 in some embodiments (i.e., fasteners 32 may, in some cases, be disposed at different locations of screen 34 each of which is no more than approximately three inches from a respective upper edge of screen 34 as measured along a phantom reference line along the screen perpendicular to the upper edge). Alternatively, fasteners 32 may be disposed at different locations of screen 34 each of which is greater than approximately three inches from a respective upper edge of screen 34 as measured along a phantom reference line along the screen perpendicular to the upper edge. In some embodiments, fasteners 32 may be disposed at different locations of screen 34 each of which is greater than approximately 12 inches from an upper edge of screen 34 as measured along a phantom reference line along the screen perpendicular to the upper edge. As described in more detail below, particularly in reference to cubicle curtains, fasteners 32 may, in some cases, be disposed at different locations of screen 34 each of which is at least approximately 20 inches from an upper edge of screen 34 as measured along a phantom reference line along the screen perpendicular to the upper edge.

Regardless of the positions of fasteners 32 from an upper edge of screen 34, fasteners 32 may be spaced any distance from each other along screen 34. In particular, although it may be advantageous for fasteners 32 to be evenly spaced across screen 34 such that screen 34 may be uniformly hung, fasteners 32 may be spaced non-evenly in some cases. In yet other embodiments, curtain 30 may include a single fastener which extends across a majority or entire width of screen 34. In some cases, fasteners 32 may be adjustable along the length and/or the width of screen 34. In particular, curtain 30 may, in some embodiments, include one or more means by which to allow fasteners 32 to be moved in the vertical and/or horizontal direction. In this way, the arrangement of fasteners 32 along screen 30 may be changed for a desired effect of curtain 30, particularly whether there is more or less of screen 30 above or below the fasteners and/or in regard to optimizing the spacings of fasteners 32 to allow curtain to hang in a desired fashion. In any case, fasteners 32 may, in some embodiments, be affixed to exterior surfaces of screen 34. Alternatively, fasteners 32 may be affixed to interior surfaces of screen 34 and extend through openings within screen 34. In yet other cases, fasteners 32 may be coupled to supports within screen 34 or supports affixed to exterior surfaces of screen 34 and, thus, fasteners 32 may not be directly affixed to screen 34 in some cases.

Regardless of the arrangement of fasteners 32 along screen 34, screen 34 may extend any distance below fasteners 32, depending on the design specifications for the curtain. As set forth in more detail below, the curtains described herein may, in some embodiments, be used to block light emitted from germicidal lamp/s of a disinfection apparatus. Similarly, in cases which the curtains described herein are used in conjunction with a disinfection apparatus having a germicidal source other than a lamp, the curtains may, in some embodiments, be used to block the germicide emitted from the germicidal source. In any of such cases, it may be advantageous for screen 34 to extend at least to an elevation below the germicidal source/s of the apparatus. Depending on the configuration of the disinfection apparatus and the height at which curtain 30 is hung, a lower edge of screen 34 may, in some embodiments, be at least approximately 1.5 feet away from fasteners 32 and, in some cases, at least approximately 3.0 feet away from fasteners 32. In yet other embodiments, screen 34 may extend to an elevation within approximately 18 inches from the floor of a room in which curtain 30 is hung, including coming into contact with the floor. Alternatively, screen 34 may not substantially extend below fasteners 32 (i.e., not more than approximately 3 inches). In particular, the object to which curtain 30 may be attached may be sufficient to block enough visible and/or UVC light generated from germicidal lamp/s of a disinfection apparatus or block enough germicide generated from non-lamp source/s of a disinfection apparatus in a region which extends below fasteners 32 and, thus, screen 34 may not need a lower section of great length (i.e., the section extending below fasteners 32) in some cases.

As noted above, the curtains described herein may be used in conjunction with cubicle curtains. As used herein, the term "cubicle curtain" refers to a hanging cloth used in a medical treatment facility that provides a private enclosure in a room. In general, cubicle curtains and/or cubicle curtain tracks are configured such that there is open and/or perforated (e.g., mesh) space extending at least approximately 20 inches from the ceiling of the room, and more specifically, between approximately 20 inches and approximately 25 inches. In particular, cubicle curtain tracks may be hung a spaced distance (i.e., at least approximately 20 inches) from a ceiling and/or cubicle curtains may include a perforated upper section of at least approximately 20 inches from an upper edge of the curtain. Additionally or alternatively, a cubicle curtain may include hooks of substantial length (e.g., between approximately 5 inches and approximately 25 inches) attached to an upper edge of the curtain. In any case, an open or perforated space near the ceiling may allow sprinkler heads exterior to an area encased by a cubicle curtain to disperse water to that area and/or allow sprinkler heads in the encased area to disperse water exterior to the area. In addition or alternatively, curtain racks suspended approximately 20 inches or more from a ceiling may allow cubicle curtains to be generally hung without a ladder.

In some cases, it may be advantageous to block an open and/or perforated space provided by a cubicle curtain or a suspended cubicle curtain rack to prevent transmission of a germicide generated on the other side of the cubicle curtain. Thus, in some embodiments, fasteners 32 may be arranged at different locations of screen 34 each of which is at least approximately 20 inches and, in some cases at least 25 inches, from a respective upper edge of screen 34 as measured along a phantom reference line along the screen perpendicular to the upper edge. In other cases, however, an open and/or perforated space provided by a cubicle curtain or a suspended cubicle curtain rack may not need to be completely blocked or blocked at all and, thus, in some embodiments, fasteners 32 may be arranged at different locations of screen 34 each of which is less than approximately 20 inches from a respective upper edge of screen 34 as measured along a phantom reference line along the screen perpendicular to the upper edge. In any case, the idea of arranging fasteners 32 at different locations of screen 34 each of which is at least approximately 20 inches from a respective upper edge of screen 34 need not be specific to use of curtain 30 as an addendum to a cubicle curtain. In particular, the placement of fasteners 32 at least 20 inches from upper edges of screen 34 may be applicable when curtain 30 is used as an addendum to other types of room dividers or when curtain 30 is to be hung independent of a room divider.

In some cases, screen 34 may be pliable such that curtain 30 may be readily bent and/or compacted. In such embodiments, it is noted that even though the term curtain is often used in reference to fabrics (i.e., woven, knitted or felted textiles), the curtains described herein are not so limited. In particular, screen 34 may include any pliable non-textile material/s and/or any pliable textile material/s. Examples of pliable materials for screen 34 include but are not limited to nylon, rayon and polyester. In yet other embodiments, screen 34 may be non-pliable or screen 34 may include a combination of pliable and non-pliable sections. Examples of non-pliable materials for screen 34 include but are not limited to metals, relatively stiff plastic materials, and wood. As discussed in more detail below, the amount of space above a room divider may vary among dividers. In order to insure the ability of the section of screen 34 above fasteners 32 to block such spaces, it may be conducive for at least the section of screen 34 above fasteners 32 to include a pliable material such that it may bend when placed in an area of lesser height than its length (i.e., when it is abutted against a ceiling of a room). As further explained below, in order to allow such suppleness, but yet have upper section of screen 34 prop up to cover the space, curtain 30 includes upper struts 38 in and/or along the upper section of screen 34. In addition to upper struts 38, the pliable material comprising the section of screen 34 above fasteners 32 may, in some cases, have a sufficient degree of stiffness to aid in preventing the portion of the screen above fastener 32 from flopping or slumping over.

In some cases, a portion or all of screen 34 may include an absorbent pliable material. More specifically, it may be advantageous for at least an upper section of screen 34, particularly the portion of screen 34 above fasteners 32, to be sufficiently water absorbent such that if sprinklers on a ceiling are activated when the curtain is being utilized, the upper section of screen 34 will move downward (e.g., fold down, collapse, etc.) by the weight of the absorbed water. Such action will open a space by which water from the sprinklers (on either side of curtain 30) may pass, possibly allowing use of the curtain to meet fire building codes and/or fire building standards. In general, screen 34 may include any absorbent pliable material. Examples of absorbent materials which may be included in screen 34 include but are not limited to sponges and hydrogel crystals incorporated into a pliable material. In any case, screen 34 may include any number of sheets of material/s, including a single sheet of material or multiple sheets layered upon each other. Each sheet may include a single type of material or multiple types of materials. In embodiments in which multiple sheets of materials are used, some or all of the sheets may include the same material/s as each other or they may include different materials.

As described in more detail below, in cases in which a disinfection apparatus having germicidal lamps is used in conjunction with curtain 30, it may be advantageous for screen 34 to include a material to attenuate a majority amount of the visible light spectrum and/or a majority amount of the ultraviolet electromagnetic radiation subtype C (UVC) light spectrum. Furthermore, in some cases, it may be advantageous for at least one side of screen 34 to be highly reflective, particularly to UVC light. In particular, it may be advantageous for at least one side of screen 34 to include a material which exhibits greater than 50% reflectance, or more specifically, greater than 85% reflectance. Examples of reflective materials which may be employed include but are not limited to metalized nylon, biaxially-oriented polyethylene terephthalate (boPET) (e.g., Mylar), and GORE® DRP® Diffuse Reflector Material available from W. L. Gore & Associates, Inc. In addition or alternative to being highly reflective, screen 34 may include a variety of other material characteristics, such as but not limited to being antimicrobial and/or fire resistant. In some cases, screen 34 may include a material which is resistant to degradation by exposure to chemical agents, particularly those which may be used for liquid, gas, vapor or plasma germicides. Such a material may be particularly suitable in embodiments in which curtain 30 is used in conjunction with a disinfection apparatus having germicidal sources other than lamps, light emitting diode (LED) solid state devices, or lasers.

As discussed above, curtain 30 may include lower struts 36 coupled to fasteners 32 and extending to an elevation below fasteners 32. In general, lower struts 36 provide a manner by which to manipulate curtain 30 such that fasteners 32 may be joined to an object for hanging curtain 30 as well as disconnecting fasteners 32 from an object when curtain 30 is taken down. In particular, lower struts 36 are compositionally and/or structurally configured such that curtain 30 may be lifted or lowered via lower struts 36 and, correspondingly, mounted or dismounted from an object, particularly to and from a surface of an object which is higher than the person manipulating curtain 30. In view thereof, each of lower struts 36 include a material composition and a structural configuration (e.g., length, width and density) which can support each of corresponding fasteners 32 and adjacent portions of screen 34 when lower struts 36 are grasped and lifted or lowered. More specifically, each of lower struts 36 may include a material composition and a structural configuration which does not yield lower struts 36 to substantially bend or compress upon application of an amount of force needed to lift or lower curtain 30. Example materials for lower struts 36 include but are not limited to metals, relatively stiff plastic materials, and wood. Examples of structural configurations may include a rod of sufficient length, width and density to prevent bending or compression of the rod when lifting or lowering curtain 30. In some cases, lower struts 36 may include mechanisms by which to manipulate fasteners to couple to an object. For example, lower struts 36 may, in some embodiments, include latches by which to open and close clasps serving as fasteners 32. Other mechanisms for other types of fasteners may be considered.

In addition to their configuration to resist deformation upon lifting and lowering curtain 30, lower struts 36 may have a length which allows a user to lift and lower curtain 30 without the need of a ladder. In particular, as noted above, curtain 30 may be used as an addendum to existing room dividers and many room dividers extend to heights greater than six feet from a floor of a room. Given height variability among people, it may be advantageous for lower struts 36 to extend to elevations at least 24 inches below fasteners 32 to ensure the suitability of curtain 30 to be easily mounted and dismounted for a variety of users. In some cases, however, lower struts 36 may extend to elevations less than 24 inches below fasteners 32. Regardless of their length, lower struts 36 may be spaced any distance along screen 34 which enables each of lower struts 36 to sufficiently support its adjoining fastener and adjacent amounts of screen 34 such that the corresponding portion of curtain 30 can be mounted and dismounted to an object. Although a spacing of approximately 1 foot to approximately 3 feet between lower struts 36 may be conducive for a user to manipulate two of the lower struts at once, narrower and wider spacings may be considered. In particular, it is noted that lower struts 36 may be manipulated individually for mounting and dismounting curtain 30. Furthermore, curtain 30 may include any number of lower struts 36, including a single lower strut or any plurality of lower struts and, thus, curtain 30 should not be restricted to the depiction in FIG. 1.

It is further noted that lower struts 36 can be coupled to screen 34, but they need not be nor do lower struts 36 need to be arranged on the same side of screen 34 as fasteners 32. In particular, in some cases, lower struts 36 may be partially or fully arranged on the opposite side of screen 34 as fasteners 32. In other embodiments, lower struts 36 may be partially or fully arranged internal to multiple sheets of screen 34 or may be arranged within pleats of screen 34. In any case, lower struts 36 may be directly coupled to fasteners 32 or they may be indirectly coupled to fasteners 32, such as via an extension rod. Furthermore, although lower struts 36 are shown in FIG. 1 extending down to the same elevation, lower struts 36 need not be so limited. In particular, one or more of lower struts 36 may extend down to different elevations than the other lower struts. In addition, although lower struts 36 may include the same material composition and structural configuration as each other, lower struts 36 are not necessarily so restricted. In particular, one or more of lower struts 36 may have different material compositions and/or structural configurations than the other lower struts. Moreover, lower struts 36 may include the same or different material composition as fasteners 32. Furthermore, the number of lower struts 36 need not equal the number of fasteners 32 as shown in FIG. 1. In particular, curtain 30 may include fewer or more lower struts 36 than fasteners 32 in some cases.

As further shown in FIG. 1, curtain 30 may include upper struts 38 coupled to screen 34 and extending to an elevation above fasteners 32. In general, upper struts 38 prop up the section of curtain 30 above fasteners 32. In particular, upper struts 38 are compositionally and/or structurally configured such that the section of curtain 30 above fasteners 32 does not flop or slump over. In some embodiments, upper struts 38 may include a substantially rigid material and/or structural configuration. In some of such cases, upper struts 38 may include the same material composition and structural configuration as lower struts 36. In other such cases, upper struts 38 may include different material compositions and/or structural configurations than lower struts 36. In yet other embodiments, upper struts 38 may be materially and structurally configured such that upper struts 38 may bend or bow, but not break if a force is applied to them, such as shown in FIG. 1. More specifically, upper struts 38 may be materially and structurally configured such that upper struts 38 may bend or bow, but not break if they are introduced into an area of lesser height than their lengths. In some of such cases, upper struts 38 may be inherently curved without having any pressure applied to them (i.e., upper struts 38 may be intrinsically convex relative to fasteners 32 as shown in FIG. 1 or, alternatively, upper struts 38 may be intrinsically concave relative to fasteners 32). In yet other embodiments, upper struts 38 may be inherently straight unless pressure is applied to them.

As mentioned above, in some embodiments, it may be advantageous to block an open or perforated space above or along an upper section of a room divider, such as commonly afforded by cubicle curtains, suspended cubicle curtain racks and other room dividers. Given the height variability of open and/or perforated spaces among different cubicle curtain configurations, it may be advantageous for upper struts 38 to have length of at least 20 inches or, in some cases, at least 22 inches to ensure the suitability of curtain 30 to block open and/or perforated spaces in a variety of scenarios. In such cases, it would be particularly advantageous for upper struts 38 to be materially and structurally configured such that they may bend, but not break upon contact with a ceiling. Example materials for upper struts 38 in such cases may be substantially pliable materials as similarly used for bike flag poles or the peripheral cord used for twisting windshield sun shades. Other materials may be considered as well. Example structural configurations for upper struts 38 which may aid in inducing a relatively low degree of stiffness is to have a relatively thin, narrow or hollow construction. Other structural configurations may be considered as well. It is noted that, in some cases, upper struts 38 may have a length less than 22 inches, more specifically less than 20 inches and, in some cases, less than 12 inches, but such relatively short lengths need not exclude the possibility of upper struts 38 to be of a pliable material and/or structural construction to make upper struts 38 supple.

In some embodiments, upper struts 38 may include a lower degree of stiffness than lower struts 36. More specifically, upper struts 38 may include different material compositions and/or structural configurations to affect a lower degree of stiffness relative to lower struts 36. In particular, a variability of stiffness among lower struts 36 and upper struts 38 may beneficially allow curtain 30 to be mounted and dismounted from an object particularly close to a ceiling. More specifically, a variability of stiffness among lower struts 36 and upper struts 38 may advantageously allow curtain 30 to be lifted and lowered without the need of a ladder by a user and yet block an entirety of a space extending up to the ceiling. Any combination of materials of differing stiffness may be used for upper struts 38 and lower struts 36, depending on the design specifications of curtain 30. In some embodiments, however, upper struts 38 and lower struts 36 may be of the same material composition but vary in stiffness. In such cases, the structural configurations of the struts may solely affect their differences in stiffness. Example structural configurations which may aid in inducing a lower degree of stiffness relative to lower struts 36 is for upper struts 38 to have a thinner, narrower, or hollow construction as compared to lower struts 36. Other structural configurations may be considered as well. In general, any degree of stiffness variability to affect the respective objectives for struts 36 and 38 may be employed (i.e., to support fasteners 32 and screen 34 such that curtain 30 may be lifted and lowered via lower struts 36 and to allow upper struts 38 to bend or bow, but not break, upon application of force thereto). Examples of variability differences may be lower struts 36 being at least 20% more stiff than upper struts 38 and, in some cases, lower struts 36 being at least 50% more stiff than upper struts 38.

Regardless of their relative stiffness, lower struts 36 and upper struts 38 may, in some embodiments, be coupled to each other, either directly or via fasteners 32. In some cases, lower struts 36 and upper struts 38 may be integral portions of a single strut. In such embodiments, fasteners 32 may be directly coupled to upper struts 38 and/or lower struts 36. Alternatively, fasteners 32 may be coupled to them via an extension rod. In yet other embodiments, lower struts 36 and upper struts 38 may be distinct components. In some of such cases, the struts may be directly coupled to each other or indirectly coupled to each other via fastener 32 and/or a connecting rod. In yet other embodiments, lower struts 36 and upper struts 38 may not be connected to each other. In any case, curtain 30 may include any number of upper struts 38, including a single upper strut or a plurality of upper struts greater or less than the four upper struts depicted in the example of FIG. 1. In some embodiments, the number of lower and upper struts in curtain 30 need not be the same. In particular, curtain 30 may include a greater quantity of lower struts 36 than upper struts 38 or vice versa. Furthermore, the spacing of upper struts 38 need not be the same as the spacing of lower struts 36. In particular, upper struts 38 may be spaced any distance along screen 34 which enable the upper section of the screen to be sufficiently upheld.

Furthermore, upper struts 38 need not be coupled to the same side of screen 34 as fasteners 32 such as shown in FIG. 1. In particular, upper struts 38 may be partially or fully arranged the opposite side of screen 34 as fasteners 32. In other embodiments, upper struts 38 may be partially or fully arranged internal to multiple sheets of screen 34 or may be arranged within pleats of screen 34. Furthermore, upper struts 38 can be coupled to screen 34, but they need not be nor do upper struts 38 need to be arranged on the same side of screen 34 as lower struts 36. In any case, although upper struts 38 are shown in FIG. 1 extending to the same elevation, upper struts 38 need not be so limited. In particular, one or more of upper struts 38 may extend to different elevations than the other upper struts. In addition, although upper struts 38 may include the same material composition and structural configuration, upper struts 38 are not necessarily so restricted. In particular, one or more of upper struts 38 may have different material compositions and/or structural configurations than the other upper struts. Moreover, upper struts 38 may include the same or different material composition as fasteners 32.

As set forth above, the components of curtain 30 may include multiple variations from what is depicted in FIG. 1. Some of such variations are depicted in FIGS. 2a-2i to further highlight the scope of the different configurations possible for curtain 30. It is noted that not all variations to curtain 30 are included in the drawings for the sake of brevity. It is further noted that the entirety of curtain 30 is not depicted in each of FIGS. 2a-2i for the sake of brevity and further to emphasize the features varied from FIG. 1. Elements of FIG. 1 that are similarly configured have been indicated using the same reference numerals in FIGS. 2a-2i. It is noted that none of the features or variations emphasized in FIGS. 2a-2i are mutually exclusive of each other and, thus, any combination of the configurations described herein for fasteners, screens, lower struts, and upper struts may be considered for a curtain.

Turning to FIG. 2a, an alternative embodiment of an upper strut is shown. In particular, upper strut 40 is show in FIG. 2a having a narrower configuration than upper strut 38 shown in FIG. 1 and, more specifically narrower than lower strut 36. Such a structural variation between upper strut 40 and lower strut 36 may affect a variation of stiffness between the struts, particularly if they are of the same material composition, but they may have different material compositions. In general, the degree by which upper strut 40 is narrower than lower strut 36 may depend on the material composition of strut 40 as well as the design specifications of curtain 30. FIG. 2b illustrates an alternative embodiment in which lower strut 42 is solid and upper strut 44 is hollow as respectively depicted by the cross-sectional views along lines A-A and B-B. As with FIG. 2a, such a structural variation between upper strut 44 and lower strut 42 may affect a variation of stiffness between the struts, particularly if they are of the same material composition. In yet other cases, both struts 42 and 44 may be hollow and the degree of hollowness may be varied between them. For instance, the upper strut may have a larger interior cavity than the lower strut. FIG. 2c illustrates yet other alternative embodiment in which upper strut 46 has a shorter length than the upper struts shown and described in reference to FIGS. 1, 2a and 2b.

It is noted that struts described in reference to FIG. 2b as well as in reference to FIGS. 1, 2a, and 2c-2i are not restricted to the lower and upper struts being cylindrical, such as depicted in FIG. 2b. In particular, the struts described herein may have any cross-sectional shape. Furthermore, the lower struts and the upper struts of a given curtain may have the same cross-sectional shape or different cross-sectional shapes. For example, the lower struts may be rods having a circular cross section and the upper struts may be substantially flat panels. Other combinations of cross-sectional shapes may be considered for the lower and upper struts as well.

As noted above, upper strut 38 and lower strut 36 of FIG. 1 need not be connected to each other. Example embodiments having an upper strut separate (i.e., not connected) to a lower strut are depicted in FIGS. 2d-2f. In addition, FIGS. 2d-2f illustrate further variations to the components of curtain 30 of FIG. 1 as set forth below. It is noted that the further variations are not mutually exclusive to having an upper strut not connected to a lower strut of the curtain. Turning to FIG. 2d, upper strut 48 is shown separate from lower strut 36 and fastener 32. In addition, upper strut 48 is shown disposed within multiple sheets of screen 34 or disposed on the opposing exterior side of screen 34, as is denoted by the outline of dotted lines for upper strut 48.

Yet another alterative embodiment is shown in FIG. 2e with upper strut 50 separate from lower strut 36 and fastener 32 but coupled to the same side of the screen, albeit different materials of the screen. In particular, FIG. 2e illustrates a screen having lower section 52 and upper section 54 of different materials to which lower strut 36 and upper strut 38 are respectively coupled. As mentioned above in reference to FIG. 1, it may be conducive for at least the section of screen 34 above fasteners 32 to include a pliable material such that it may bend when placed in an area of lesser height than its length (i.e., when it is abutted against a ceiling of a room). As such, for the embodiments of FIG. 2e, it may be generally prudent to have section 54 comprise pliable material/s.

Section 52, on the other hand, may include pliable and/or non-pliable material/s. In cases in which both sections of the screen comprise pliable materials, upper section 54 may have a higher degree of stiffness than lower section 52 or vice versa.

Another embodiment in which upper strut 50 is shown separate from lower strut 36 and fastener 32 is shown in FIG. 2f. In particular, FIG. 2f illustrates upper strut 50 coupled to screen 56, which does not extend substantially below fastener 32. As noted above, such a curtain configuration may be suitable in cases in which a room divider to which the curtain is attached may be sufficient to block enough visible and/or UVC light generated from germicidal lamps of a disinfection apparatus or block enough germicide generated from non-lamp source/s of a disinfection apparatus. Thus, in such cases, a lower section of a screen below fasteners 32 may not be needed.

In some embodiments, a curtain having one or more of the features described herein may not include an upper strut. Examples of such embodiments are shown in FIGS. 2g and 2h. In particular, FIG. 2g illustrates a curtain with fastener 32 affixed to lower section 52 of a screen and having lower strut 36 extending to an elevation below fastener 32. The curtain further includes upper section 58 extending to an elevation above fastener 32, but the curtain is absent of an upper strut. In general, upper section 58 may include a material of sufficient stiffness such that portion of the screen above fastener 32 may be propped up without use of an upper strut. In some cases, upper section 58 may be a substantially rigid material, but in other cases upper section 58 may include a pliable material. Similar to the example embodiment discussed in reference to FIG. 2e, upper section 58 may include a different material composition than lower section 52 in some cases. In some embodiments, upper section 58 may have a higher degree of stiffness than lower section 52, but in other cases, upper section 58 may have a lower degree of stiffness than lower section 52. Another example of a curtain without an upper strut is shown in FIG. 2h with fastener 62 affixed near or at the upper edge of screen 60 and lower strut 64 extending to an elevation below fastener 62. In addition, fastener 62 and lower strut 64 are shown in FIG. 2h to illustrate that the material composition and/or the delineation between a fastener and lower strut may be varied among the different embodiments of curtains described herein, depending on the design of the components selected.

As noted above, lower struts 36 of FIG. 1 may be coupled to fasteners 32 such that the lower struts may aid in mounting and dismounting curtain 30 on an object. Although lower struts 36 may be directly coupled to fasteners 32 as shown in FIG. 1, the curtains described herein are not necessarily so limited. In particular, a curtain may have lower struts indirectly coupled to fasteners. An example configuration of lower struts indirectly coupled to fasteners is illustrated in FIG. 2i. In particular, FIG. 2i depicts lower struts 68 indirectly coupled to fasteners 62 via rod 66. It is noted that the number of lower struts 68 and fasteners 62 need not be equal but they can be and the spacings between the plurality of each component need not be the same but they can be. Other indirect coupling configurations may be considered as well. It is further noted that lower struts 68, fasteners 62 and rode 66 are not shown with a screen or upper struts to simplify the drawing, but such components may be compiled together to comprises a curtain.

Lastly, an alternative configuration for curtain 30 of FIG. 1 is depicted in FIG. 2j. In particular, FIG. 2j illustrates an embodiment with handle 72 extending from lower strut 70, which is coupled to fastener 62. It is noted that any handle configuration known in the art may be considered for the curtains described herein and, thus, the idea a lower strut including a handle should not be restricted to the depiction of FIG. 2j. As denoted by the dotted lines outlining fastener 62, fastener 62 is coupled to one side of screen 60 and lower strut 70 and handle 72 are arranged on an opposing side of screen 60. In any alternative configuration, lower strut 70 may be arranged on the same side of screen 60 as fastener 62 and handle 72 may alone extend into an opposing side of screen 60. In yet other configurations, lower strut 70 may be arranged internal to screen 60. As similarly described for lower struts 36 in reference to FIG. 1, it may be advantageous to have handle 72 disposed on an opposing side of screen 34 as fasteners 62. In particular, such a configuration may allow an individual grasping handle 72 on one side of curtain 60 to more easily mount the curtain in a forward motion away from the individual's body or at least make mounting the curtain in such a manner more intuitive. In yet other cases, curtain 60 may be mounted in a backward motion toward the body of the individual mounting the curtain. In such embodiments, it may be advantageous for handle 72 to be disposed on the same side of screen 34 as fasteners 62. In any case, as noted above, the features described in reference to FIGS. 1-2j are not mutually exclusive. As such, any of the configurations described in reference to FIGS. 1-2i may include handle 72 or some variation thereof.

As noted above, curtain 30 may be used as an addendum to existing room dividers. More specifically, the curtains described herein are particularly directed to facilitating attachment to edges of room dividers which are disposed at least four feet from a floor of a room and, in some embodiments, facilitating attachment to edges of room dividers which are disposed at least four feet from a floor of a room. In some cases, the room divider may be a cubicle curtain 73 hung from a curtain track 74 suspended from a ceiling 75 of the room as shown in FIG. 3a. In some of such embodiments, as illustrated in FIG. 3a, the edge to which one of the curtains described herein may be attached may be the edge of curtain track 74. Alternatively, the edge to which one of the curtains described herein may be attached may be an edge of cubicle curtain 73.

In some cases, a room divider which may be used to hang one of the curtains described herein may be a cubicle curtain 76 hung from a curtain track 77 directly mounted to a ceiling 75 of the room. In such cases, the edge to which one of the curtains described herein may be attached may be an edge of cubicle curtain 76 as shown in FIG. 3b, including any edges of the perforations of a mesh area comprising a top section of cubicle curtain 76 or an upper edge of the solid portion of the cubicle curtain. In yet other embodiments, a room divider which may be used to hang one of the curtains described herein may be a floor-based partition 78 having an uppermost surface 79 spaced from a ceiling of the room. In such cases, the edge to which one of the curtains described herein may be attached may be upper edge 79 of floor based partition 78 as shown in FIG. 3c. Alternatively, an edge of an opening within a floor based partition may be used to hang one of the curtains described herein.

As further noted above, the curtains described herein may, in some embodiments, be used to block light emitted from germicidal lamp/s of a disinfection apparatus or block germicide generated from non-lamp source/s of a disinfection apparatus. In particular, the curtains described herein may include screens configured to block visible light and/or ultraviolet light and, more specifically, to attenuate a majority amount of the visible light spectrum and/or a majority amount of the UVC light spectrum. In addition or alternatively, the curtains described herein may include screens configured to block non-light germicide. In particular, the curtains described herein may include a material to withstand repeated exposure to a germicide without disintegrating or losing its ability to substantially block transmission of the germicide therethrough.

In view of being used together with a disinfection apparatus, any of the curtains described herein may comprise a system having a disinfection apparatus with a germicidal source. An example of such a system is illustrated in FIG. 4. In particular, FIG. 4 depicts system 80 including disinfection apparatus 82 and curtain 84. Curtain 84 may include any of the curtains described herein or, more specifically, may include a curtain having any of the features described in reference to FIGS. 1-2i. In some cases, disinfection apparatus 82 may include a storage compartment for curtain 84. In general, disinfection apparatus 82 may be configured for room disinfection. More specifically, disinfection apparatus 82 may be configured to expose areas and rooms as well as objects as a whole to a germicide and, thus, is specifically configured to distribute a germicide in a spacious manner to an ambient of a room in which the disinfection apparatus is arranged. Disinfection apparatus 82 may be of any shape, size, or configuration in which to achieve such objectives. In any case, optional features for the disinfection apparatuses considered herein include wheels and/or a handle to affect portability for the apparatus. In addition or alternatively, a disinfection apparatus may be configured to determine whether people are present in the area enclosed by the accompanying curtain, such as by motion detection or photo recognition. In addition or alternatively, a disinfection apparatus may include a central processing unit to execute program instructions associated with operations of the apparatus. Any of such optional features (i.e., wheels, a handle, a room occupancy sensor and a central processing unit) may be disposed within or on a support structure of the ultraviolet disinfection apparatus which supports the discharge lamp of the apparatus.

Disinfection apparatus 82 may include one or more germicidal sources, depending on the design specifications of the apparatus. The term "germicidal source" as used herein refers to a collection of one or more components used to generate and disperse a germicidal agent, and, if applicable, is inclusive to any additional components used to effect the generation or dispersal of the germicidal agent. In some embodiments, a device or an apparatus may include a single set of components for generating a germicide. In such cases, the components associated with generating the germicide may be referred to as the germicidal source or, alternatively, the device or apparatus as a whole may be referenced as a germicidal source. In other embodiments, a device or apparatus may include multiple germicidal sources (i.e., multiple sets of components for generating multiple sources of one or more germicides). In any case, the germicidal sources considered for disinfection apparatus 82 may be of any size and shape, depending on the design specifications of the apparatuses. The term "germicide" as used herein refers to an agent for deactivating or killing microorganisms, particularly disease carrying and/or disease producing microorganisms (a.k.a., germs). The term "kill," as used herein, means to cause the death of an organism. The term "deactivate," as used herein, means to render an organism unable to reproduce without killing. As such, a germicide which is configured to deactivate a microorganism refers to an agent which renders a microorganism unable to reproduce but leaves the organism alive.

In general, the germicidal source/s of disinfection apparatus 82 may be configured to generate and/or disperse a germicide in form of a liquid, a vapor, a gas, a plasma, ultraviolet light, and/or high-intensity narrow-spectrum (HINS) light. Examples of disinfection sources which may be configured to disperse liquid, vapor, gaseous, or plasma germicides include but are not necessarily limited to liquid sprayers, foggers, plasmas torchers and misting systems including wet and dry mist systems. As used herein, the term "mist" refers to a suspension of minute globules of a liquid in a gas. For use herein, a germicidal mist is categorized as a liquid germicide. Examples of disinfection sources which may be configured to generate ultraviolet light and/or high-intensity narrow-spectrum (HINS) light include discharge lamps, light emitting diode (LED) solid state devices, and excimer lasers. In some embodiments, a germicidal light source may generate ranges of light which are not germicidal such as but not limited to visible light, but such capability will not deter from the reference of the light sources being germicidal.

A discharge lamp as used herein refers to a lamp that generates light by means of an internal electrical discharge between electrodes in a gas. The term encompasses gas-discharge lamps, which generate light by sending an electrical discharge through an ionized gas (i.e., a plasma). The term also encompasses surface-discharge lamps, which generate light by sending an electrical discharge along a surface of a dielectric substrate in the presence of a gas, producing a plasma along the substrate's surface. As such, germicidal light sources which may be considered for disinfection apparatus 82 include gas-discharge lamps as well as surface-discharge lamps. Discharge lamps may be further characterized by the type of gas (or gases) employed and the pressure at which they are operated. The discharge lamps which may be considered for disinfection apparatus 82 include those of low pressure, medium pressure and high intensity. In addition, the gas (or gases) employed may include helium, neon, argon, krypton, xenon, nitrogen, oxygen, hydrogen, water vapor, carbon dioxide, mercury vapor, sodium vapor and any combination thereof. In addition, discharge lamps considered for disinfection apparatus 82 may include those which generate continuous light and/or those which generate light in short durations, the latter of which are referred to herein as flashtubes or flashlamps. Flashtubes or flashlamps that are used to supply recurrent pulses of light are referred to herein as pulsed light sources.

A commonly used gas-discharge lamp used to produce continuous light is a mercury-vapor lamp, which may be considered for disinfection apparatus 82. It emits a strong peak of light at 253.7 nm, which is considered particularly applicable for germicidal disinfection and, thus, is commonly referenced for ultraviolet germicidal irradiation (UVGI). A commonly used flashlamp which may be considered for disinfection apparatus 82 is a xenon flashtube. In contrast to a mercury-vapor lamp, a xenon flashtube generates a broad spectrum of light from ultraviolet to infrared and, thus, provides ultraviolet light in the entire spectrum known to the germicidal (i.e., between approximately 200 nm and approximately 320 nm) as well as visible light. In addition, a xenon flashtube can provide relatively sufficient intensity in the spectrum which is known to be optimally germicidal (i.e., between approximately 260 nm and approximately 265 nm). Moreover, a xenon flashtube generates an extreme amount of heat, which can further contribute to the deactivation and killing of microorganisms.

Furthermore, a surface-discharge lamp may be considered for disinfection apparatus 82 as noted above. Similar to a xenon flashtube, a surface-discharge lamp produces ultraviolet light in the entire spectrum known to the germicidal (i.e., between approximately 200 nm and approximately 320 nm) as well as visible light. In contrast, however, surface-discharge lamps operate at higher energy levels per pulse and, thus, greater UV efficiency, as well as offer longer lamp life as compared to xenon flashtubes. It is noted that the aforementioned descriptions and comparisons of a mercury-vapor lamp, a xenon flashlamp, and a surface discharge lamp in no way restrict disinfection apparatus 82 to include such lamps. Rather, the aforementioned descriptions and comparisons are merely provided to offer factors which one skilled in the art may contemplate when selecting a discharge lamp for a disinfection apparatus, particularly depending on the objective and application of the apparatus.

As noted above, the germicidal source/s of disinfection apparatus 82 may be configured to generate and/or disperse a germicide in form of a liquid, vapor, gas, or plasma. In some embodiments, a liquid, vapor, gaseous, or plasma germicide may impart its deactivation or killing functionality by the manner in which it is used. For example, boiling water, steam and heated air are often effective sterilizing agents due to the temperature at which they are employed. Furthermore, the germicidal effectiveness of some plasma germicides is primarily due to the presence and activity of charged particles making up the plasma rather than the molecular composition of the charged particles. As used herein, the phrase "molecularly configured" refers to the elemental composition of a substance (i.e., the number and type of atoms making up a substance) to impart the function stated after the phrase. In some cases, the functionality of a liquid, vapor, gaseous or plasma germicide to deactivate and/or kill a microorganism may be attributed to the elements constituting the germicide and, thus, such germicides may be referenced as being molecularly configured to deactivate and/or kill microorganisms.

An example of a gaseous germicide that is molecularly configured to kill microorganisms is ozone. Examples of plasmas germicides that are molecularly configured to deactivate or kill microorganisms are those that employ or generate reactive oxygen species. Examples of liquid and vapor germicides that are molecularly configured to deactivate or kill microorganisms include liquid and vapor disinfection solutions having a principle disinfection agent such as but not limited to bleach, hydrogen peroxide, chlorine, alcohol, quaternary ammonium compounds or ozone. In any of such cases, the liquid and vapor germicides may be aqueous or non-aqueous. It is noted that the disinfection source/s considered disinfection apparatus 82 may include those which are configured to impart deactivation or killing functionality by the manner in which the germicide is used as well as by a germicide's molecularly configuration.

Figure 5A:
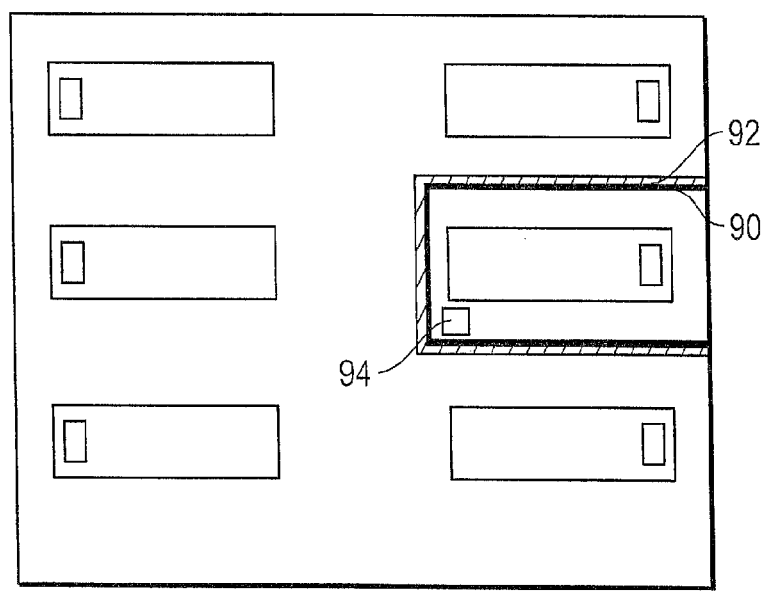
FIGS. 5a-5c illustrate example uses of auxiliary curtains attached to cubicle curtains of multiple occupancy patient rooms.
Figure 5B:
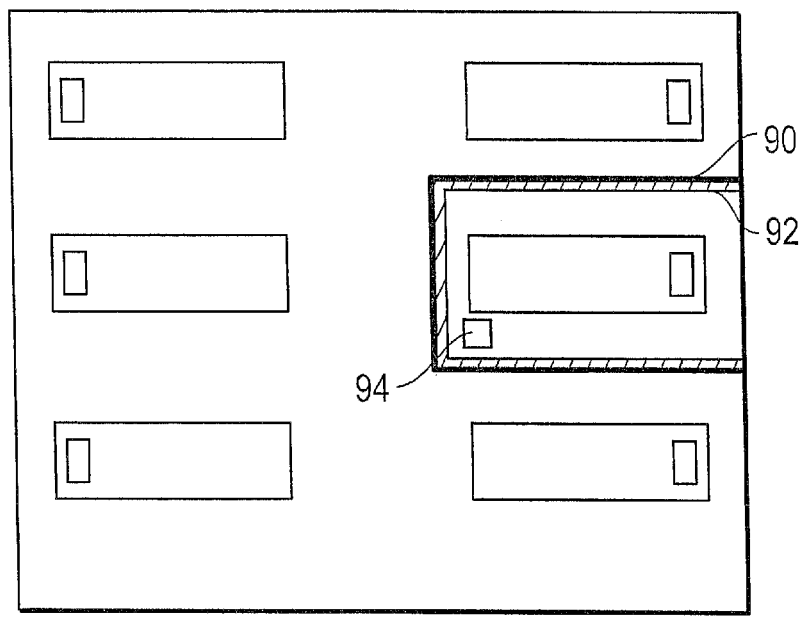
Figure 5C:
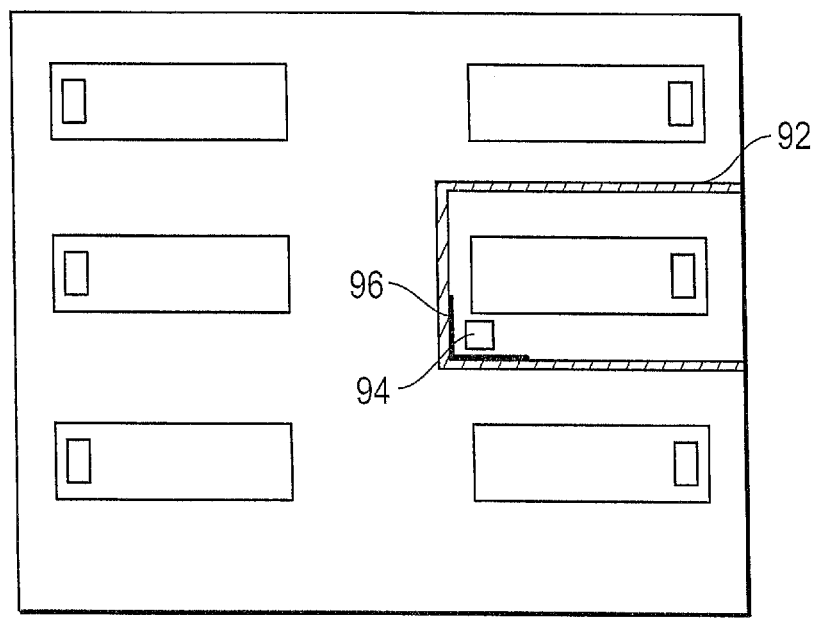

Examples of using one of the curtains described herein in conjunction with a germicidal disinfection apparatus are shown in FIGS. 5a-5c. In particular, FIG. 5a illustrates a top view of a multiple occupancy patient room with curtain 90 hanging on an interior side of cubicle curtain 92 which is drawn around a single patient bed. Disinfection apparatus 94 is also disposed within the space enclosed by the cubicle curtain. Disinfection apparatus 94 may include any of the germicidal sources and features described above for disinfection apparatus 82. Due to the containment provided by curtain 90 and cubicle curtain 92, disinfection apparatus 94 may be operated in the space without exposing occupants of the room exterior to the space to high levels and/or intensity of a germicide and/or, in the case disinfection apparatus 94 include a germicidal light source, high levels or intensity of visible light. In some cases, disinfection apparatus 94 may be operated at multiple locations within the space enclosed by the curtains in order to insure all side of the bed are disinfected. However, in cases in which disinfection apparatus includes a germicidal light source, multiple operations of disinfection apparatus 94 may be advantageously avoided when the side of curtain 90 interior to the enclosed space comprises a material of relatively high reflectance (e.g., 50% or more). In an alternative embodiment, curtain 90 may be hung on the exterior side of cubicle curtain 92 as shown in FIG. 5b. In particular, FIG. 5b illustrates a top view of a multiple occupancy patient room with curtain 90 hanging on an exterior side of cubicle curtain 92 drawn around a single patient bed. As shown in FIG. 5b, disinfection apparatus 94 is disposed within the space enclosed by the cubicle curtain.

It is noted that the curtains described herein need not cover an entirety of a room divider. In particular, in some cases, partial coverage may only be needed. An example of an embodiment in which one of the curtains described herein is attached to only a portion of a cubicle curtain is shown in FIG. 5c. In particular, FIG. 5c illustrates a top view of a multiple occupancy patient room with curtain 96 hanging on an interior side of cubicle curtain 92 drawn around a single patient bed. As shown, curtain 96 is hung in the vicinity of disinfection apparatus 92, which is also disposed within the space enclosed by cubicle curtain 92. In some cases, the intensity of germicide and/or visible light emitted from disinfection apparatus 94 may dissipate enough in a short distance from the disinfection apparatus such that much of cubicle curtain 92 may be sufficient to block the germicide and/or visible light to a tolerable level for occupants exterior to the space enclosed by the cubicle curtain. In such cases, it may only be necessary or desirable to block the portion of cubicle curtain 92 adjacent to disinfection apparatus 94, such as shown by curtain 96 in FIG. 5c. It is noted that curtain 96 may be hung on the interior or exterior of cubicle curtain 92 and is not restricted to corners of enclosed spaces. In addition, the idea of partially covering a room divider need not be restricted to cubicle curtains, but may extend to any room divider. Thus, the scope of using a curtain to partially cover a room divider should not be restricted to the depiction of FIG. 5c.

Figure 6:
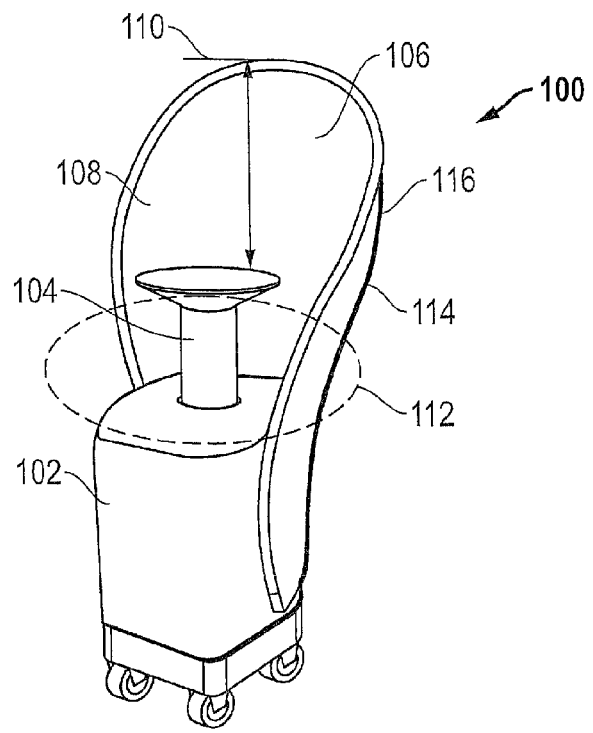
FIG. 6 illustrates a disinfection apparatus with a shield partially surrounding a germicidal source.

In yet other cases, a disinfection apparatus may be configured to block emitted germicide or visible light in a given direction or region adjacent the apparatus. An example of such a disinfection apparatus is depicted in FIG. 6. In particular, FIG. 6 illustrates disinfection apparatus 100 including support structure 102 supporting germicidal source 104 and shield 106 attached to the support structure and arranged to block germicide and/or light emitted from germicidal source 104 from an area adjacent to disinfection apparatus 100. In general, germicidal source 104 may be configured to generate and/or disperse a germicide in form of a liquid, a vapor, a gas, a plasma, ultraviolet light, and/or high-intensity narrow-spectrum (HINS) light as similarly described for the germicidal source/s of disinfection apparatus 82. In addition, shield 106 may generally be configured to block germicide and/or light projected from germicidal source 104 from an area adjacent disinfection apparatus 100. For example, in cases in which germicidal source 104 is a germicidal light source, shield 106 may be configured to block a majority amount of the visible light spectrum and/or a majority amount of the ultraviolet electromagnetic radiation subtype C light spectrum. In some of such cases, side 108 of shield 106 facing germicidal source 104 may include a material which exhibits greater than 50% reflectance, or more specifically, greater than 85% reflectance.

Regardless of the type of germicide germicidal source 104 is configured to generate and/or disperse, germicidal source 104 may generally be arranged within disinfection apparatus 100 to emit a germicide and/or light into an ambient of a room in which the disinfection apparatus is arranged and, more specifically, may be arranged such that the germicide and/or light is propagated to a region which encircles the apparatus. For example, one manner of achieving such an objective when germicidal source 104 is a discharge lamp is to have the germicidal lamp arranged lengthwise and perpendicular to a horizontal plane of disinfection apparatus 100, such as shown for germicidal source 104 in FIG. 6. The discharge lamp, however, may be arranged in other manners to achieve such an objective and/or disinfection apparatus 100 may include multiple germicidal light sources, including but not limited to discharge lamps to achieve such an objective. Similar configurations may be considered for other type of germicidal sources as well.

As shown in FIG. 6, shield 106 may extend to a first elevation 110 above germicidal source 104 and may border at least one third of a continuous ring region 112 surrounding the germicidal source. Although the height of the first elevation may vary depending on the design of disinfection apparatus 100, an exemplary elevation, particularly for the disinfection apparatus shown in FIG. 6 may be at least two feet above germicidal source 104. In some cases, side 108 of shield 106 facing germicidal source 104 may be concave. In other embodiments, side 108 may be slanted or substantially upright. As shown in FIG. 6, portion 114 of shield 106 above support structure 102 may arc away from support structure 102 and may extend up to a second elevation 116 above germicidal source 104 but below the first elevation 110. Although the height of the second elevation 116 may vary depending on the design of disinfection apparatus 100, an exemplary elevation, particularly for the disinfection apparatus shown in FIG. 6 may be at least one foot above germicidal source 104. As further shown in FIG. 6, at least a portion of shield 106 above the second elevation 116 may arc back in the opposite direction. It is noted that other shield configurations may be considered for a disinfection apparatus, particularly to block emitted light in a given direction or region adjacent the apparatus.

Figure 7:
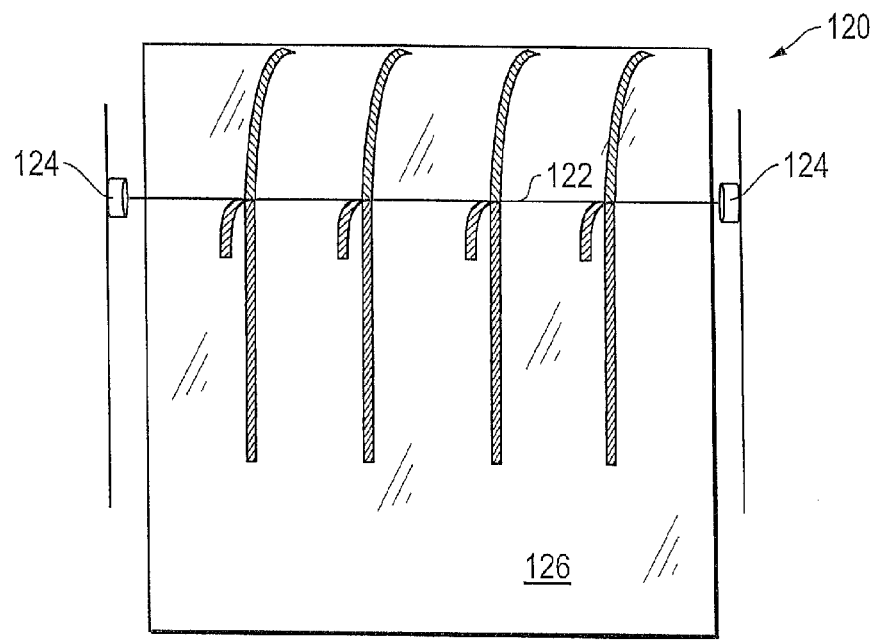
FIG. 7 illustrates an example of a room divider that is easily assembled and dissembled.

The aforementioned discussions of curtains and systems employing such curtains have been emphasized to be used in conjunction with existing room dividers, e.g., cubicle curtains or floor-based partitions. Some areas, however, may not be conducive to having room dividers that are installed and/or are bulky occupying space. For example, relatively large high traffic areas with ambiguous boundaries, such as to nurses' stations in hospitals, may not be conducive to having room dividers that are installed and/or bulky. Due to their high traffic and/or occupancy, however, it may be desirable to disinfect at least portions of such areas occasionally. FIG. 7 illustrates an example of a room divider which may be particularly suitable for such areas. In particular, FIG. 7 shows room divider 120 including one or more cords 122 and a plurality of devices 124 for supporting the one or more cords.

In general, each of devices 124 either has one of the cords attached thereto or is configured to receive attachment of one of the cords. Although it is not necessary, it may be advantageous in some cases for at least one of devices 124 to have a cord wrap or a cord reel. In some embodiments, one or more of devices 124 may be configured to retract a cord attached thereto. Alternative to cord 122 and cord bearing devices 124, room divider 120 may, in some cases, include one or more poles and a plurality of devices for supporting the one or more poles. In such cases, each of devices may either have one of the poles attached thereto or may be configured to receive attachment of one of the poles.

Regardless of whether room divider 120 includes cord/s or poles, the devices supporting the cord/s or poles may be free-standing units (e.g., poles or columns) in some embodiments. In addition or alternatively, the devices supporting the cord/s or pole/s may be configured to be mounted to a wall, a door or some other set location of a room (e.g., a cabinet). In some of such cases, the devices may be secured to a location (e.g., nailed, screwed or adhered) such that it is not removed without an intervening tool. For instance, an example of a device mounted to a wall via screws is a retractable single line cord reel often used for a clothes line. In other cases, the device may be suctioned to a location and the device may include a suction release valve for decoupling the device without having to necessarily use an intervening tool. In yet other cases, the device may include two portions, specifically a base portion which is anchored to a set location in a room (e.g., nailed, screwed or adhered) such that it is not removed without an intervening tool and a secondary portion which has a quick-release feature for connection and disconnection from the base portion. In such cases, the secondary portion has one of the cords or poles attached thereto or is configured to receive attachment of one of the cords or poles. Any quick release feature known in the art may be used for the secondary portion. Examples of quick release features includes but art not limited to mating magnets respectively within the base and secondary portion, a clamp with a quick release lever, and notches or rods configured to receive or engage and secure rods or notches of the base portion.

Regardless of the configuration of the devices used to hold the cords or poles of room divider 120, room divider 120 includes curtain 126 and a means for attaching the curtain to a cord or pole suspended between two supporting devices. In general, curtain 126 and the means for attaching the curtain to the suspended cord or pole may include any of the curtains described herein. Alternatively curtain 126 and the means for attaching the curtain to the suspended cord or pole may include any combination of a screen and a fastener by which to hang the screen, including embodiments in which the screen and fastener are coupled together or are independent of each other. Lastly, room divider 120 may include a means for affecting mobility of the devices 124 together, particularly when the devices are configured for relatively quick release from a mounting location. Examples of such a means include but is not limited to a cart configured to hold devices 124, a means for detachably adjoining devices 124 together, an any combination thereof. In some cases, devices 124 may be disposed on rollers to affect mobility. In other embodiments, devices 124 may be easily lifted into a cart or storage container. In yet other cases, devices 124 may be small enough to be transported by hand, such as when they are a quick release wall mountable retractable single line cord reel.

Figure 8:
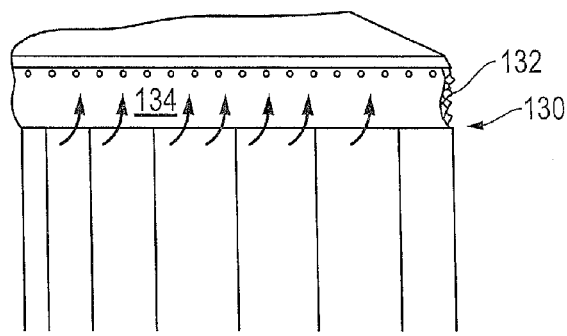
FIGS. 8-11 illustrate auxiliary curtains and devices for blocking open or perforated areas of cubicle curtains.

Alternative curtain containment devices are shown in FIGS. 8-12 and described in more detail below. It is noted that any of these devices may be used in conjunction with a disinfection apparatus for the disinfection of a region in a room. Turning to FIG. 8, cubicle curtain 130 is shown with mesh section 132 and moveable flap 134 configured to block mesh section 132. In particular, moveable flap 134 is secured to a base of mesh section 132 and includes fasteners 136 at or near its upper edge such that moveable flap 134 may be secured at the top of mesh section 132 and/or the top of cubicle curtain 130. Moveable flap 134 include a flaccid material such that it hangs below mesh section 132 when it is not fastened above the mesh section. It is noted that moveable flap 134 may be used for cubicle curtains without a mesh section, but rather just provide an open space to the ceiling.

Figure 9:
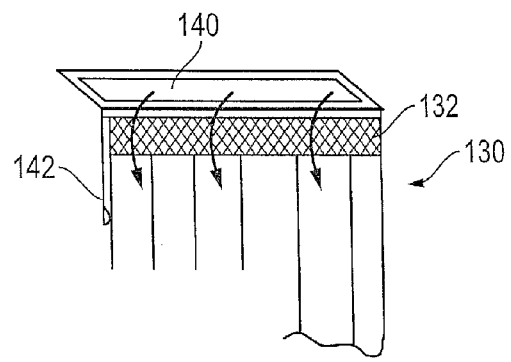

An alternative device for blocking an open and/or perforated area of a cubicle curtain is depicted in FIG. 9. In particular, FIG. 9 illustrates flip shield 140 arranged adjacent to an upper edge of cubicle curtain 130. Flip shield 140 may be coupled to the ceiling track from which cubicle curtain 130 hangs or may be coupled to a separate mounting device on the ceiling adjacent to the cubicle curtain track. In either case, the place flip shield 140 is coupled serves as a pivot point to move the shield down to block mesh section 132 (or a corresponding open area above cubicle curtain 130) or move the shield up to allow fluid passage through mesh section 132. As shown in FIG. 9, flip shield 140 includes pull cord 142 to affect the aforementioned movement of the flip shield. Flip shield 140 includes a material of sufficient stiffness such that the shield may be upheld (such that it is does not slump or flop over to cover mesh section 132). The stiff material may be confined to the ridge of the shield, may be confined to the body of the shield surrounded by its ridge, or both.

Figure 10:
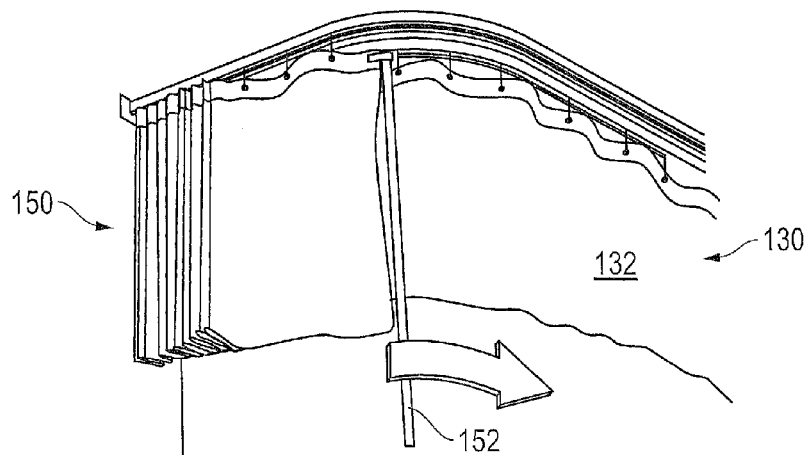
Figure 11:
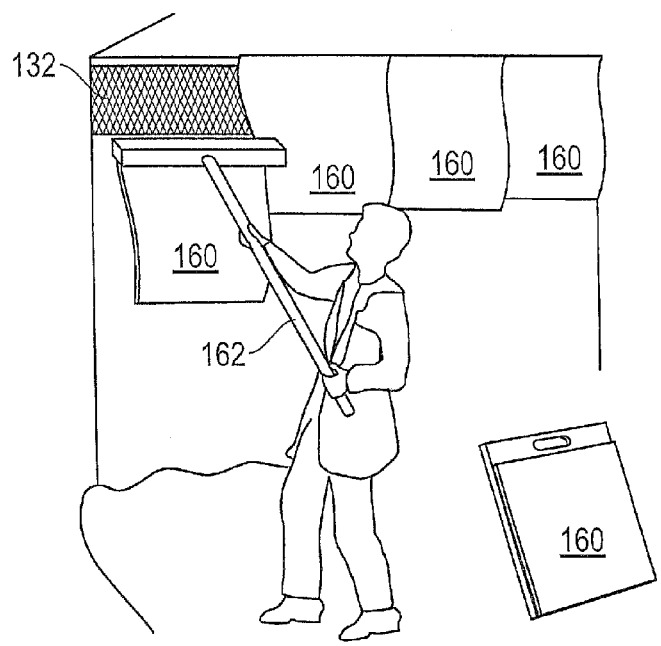

Yet another alternative device for blocking an open and/or perforated area of a cubicle curtain is depicted in FIG. 10. In particular, FIG. 10 illustrates auxiliary curtain 150 adjacent to cubicle curtain 130. In general, auxiliary curtain 150 may be disposed in the curtain track of cubicle curtain 130 or in a separate curtain track adjacent to the cubicle curtain track. As shown in FIG. 10, the material of auxiliary curtain 150 may have the same or slightly larger height than mesh section 132. In addition, auxiliary curtain 150 may include pull rod 152 to affect movement of the curtain along its curtain track by a user. In this manner, auxiliary curtain 150 may be selectively drawn to block mesh section 132 (or a corresponding open area above cubicle curtain 130). FIG. 11 illustrates yet another system for blocking an open and/or perforated area of a cubicle curtain. In particular, FIG. 11 shows a system which includes plurality of attachable sheets 160, which may be affixed to a curtain track of a cubicle curtain. The attachment means of sheet 160 may be adhesive (possibly re-adherable adhesive, such as low tack, pressure-sensitive adhesive) or magnets. As shown in FIG. 11, the system may include mounting pole 162 for a user to grasp individual sheets and attach them to a cubicle curtain track. Similar to auxiliary curtain 150 of FIG. 10, sheets 160 may have the same or slightly larger height than mesh section 132 such that mesh section 132 (or a corresponding open area above cubicle curtain 130) may be blocked by sheets 160.

Figure 12:
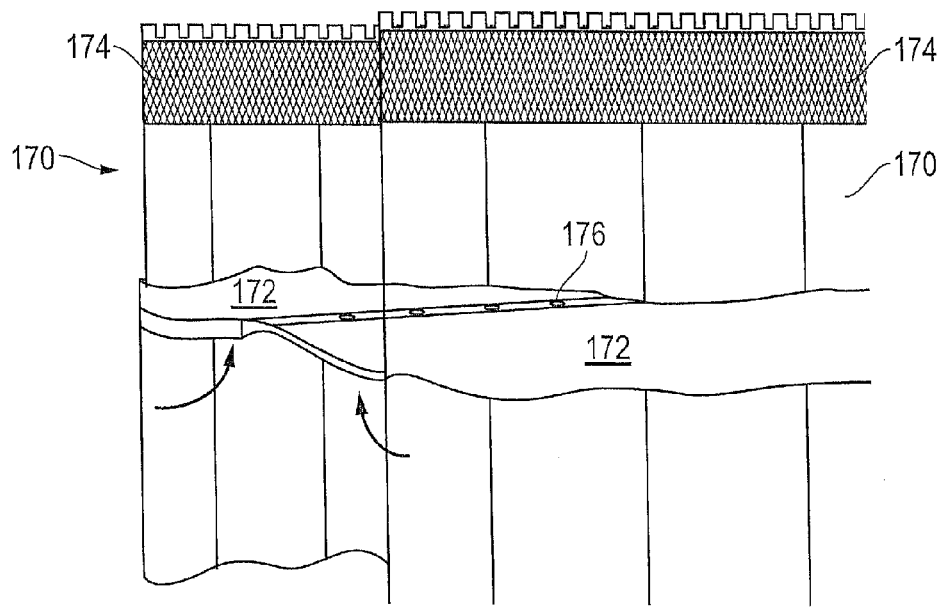
FIG. 12 illustrates opposing cubicle curtains each having a moveable flap arranged below their open and/or perforated section and attached to each other.

FIG. 12 illustrates yet other system for containing light in a confined area. In particular, FIG. 12 shows opposing cubicle curtains 170 each having a moveable flap 172 attached along a portion of the cubicle curtains below their open and/or perforated section 174. Although FIG. 12 shows moveable flaps 172 attached at approximately the mid-portion of cubicle curtain 170, the position of moveable flaps is not so limited. As shown in FIG. 12, moveable flaps 172 are attached widthwise relative to cubicle curtains 170 and are configured to join together when moved to be perpendicular with cubicle curtains 170. In particular, moveable flaps 172 includes fasteners 176 at or near their distal ends such that moveable flaps 172 may be secured together and, effectively block light from propagating above the flaps. Moveable flaps 172 generally include a flaccid material such that they hang along the side of cubicle curtains 170 when they are not fastened together.

It will be appreciated to those skilled in the art having the benefit of this disclosure that this invention is believed to provide containment curtains and, more specifically but not limited to, containment curtains for rooms which typically have multiple occupancy as well as systems and apparatuses including such containment curtains. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. The term "approximately" as used herein refers to variations of up to +/−5% of the stated number.

What is claimed is:

1. A curtain, comprising:
   a pliable screen;
   a fastener arranged along the pliable screen, wherein the fastener is configured for attaching the curtain to an object;
   a lower strut coupled to the fastener and extending to an elevation below the fastener; and
   an upper strut coupled to the pliable screen, wherein the upper strut extends to an elevation above the fastener, and wherein the upper strut comprises a lower degree of stiffness than the lower strut.

2. The curtain of claim 1, wherein the lower and upper struts comprise different materials to affect their differences in stiffness.

3. The curtain of claim 1, wherein the lower and upper struts comprise different structural configurations to affect their differences in stiffness.

4. The curtain of claim 1, wherein the lower and upper struts are integral portions of a single strut.

5. The curtain of claim 1, wherein the lower and upper struts are distinct components coupled to each other.

6. The curtain of claim 1, wherein the lower and upper struts are not connected to each other.

7. The curtain of claim 1, wherein the fastener is one of a plurality of fasteners arranged along the pliable screen for attaching the curtain to an object, wherein the lower strut is one of a plurality of struts that are individually coupled to one or more of the plurality of fasteners, wherein the plurality of struts are spaced along the pliable screen, and wherein the plurality of struts extend to one or more elevations below the plurality of fasteners.

8. The curtain of claim 1, wherein the upper strut is one of a plurality of struts which are coupled to the pliable screen and which extend to one or more elevations above the fastener.

9. The curtain of claim 1, wherein the lower strut is at least 20% more stiff than the upper strut.

10. The curtain of claim 1, wherein a length of the upper strut is greater than approximately 20 inches.

11. The curtain of claim 1, wherein a length of the lower strut is greater than approximately 24 inches.

12. The curtain of claim 1, wherein an exterior side of the pliable screen comprises a material exhibiting greater than 85% reflectance.

13. A system, comprising:
- a room divider having an edge disposed at least four feet from a floor of a room; and
- an auxiliary curtain attached to the edge via one or more fasteners, wherein the auxiliary curtain comprises:
  - one or more struts coupled to the one or more fasteners and extending to an elevation at least 24 inches below the one or more fasteners; and
  - a section of material extending to an elevation at least 3 inches above the one or more fasteners.

14. The system of claim 13, wherein the room divider is a cubicle curtain hung from a curtain track suspended from a ceiling of the room, and wherein the edge is an edge of the curtain track or an edge of the cubicle curtain.

15. The system of claim 13, wherein the room divider is a cubicle curtain hung from a curtain track directly mounted to a ceiling of the room, and wherein the edge is an edge of the cubicle curtain.

16. The system of claim 13, wherein the room divider is a floor-based partition having an uppermost surface spaced from a ceiling of the room.

17. The system of claim 13, wherein the section of material extends to an elevation at least 12 inches above the one or more fasteners.

18. The system of claim 13, wherein the room divider surrounds a space, and wherein the auxiliary curtain is disposed on a side of the room divider interior to the space.

19. The system of claim 13, wherein the room divider surrounds a space, and wherein the auxiliary curtain is disposed on a side of the room divider exterior to the space.

20. The system of claim 13, further comprising a disinfection apparatus disposed within a space enclosed by the room divider, wherein the auxiliary curtain is attached to a less than whole portion of the room divider in the vicinity of the disinfection apparatus.

21. A room divider, comprising:
- one or more cords or poles;
- one or more devices for supporting the one or more cords or poles, wherein each of the one or more devices has one of the cords or poles attached thereto or is configured to receive attachment of one of the cords or poles; and
- a curtain comprising:
  - a pliable screen;
  - a fastener disposed along the pliable screen, wherein the fastener is configured for attaching the curtain to one of the cords or poles;
  - a lower strut coupled to the fastener and extending below the fastener; and
  - an upper strut coupled to the pliable screen, wherein the upper strut extends to an elevation above the fastener.

22. The room divider of claim 21, wherein at least one of the one or more devices comprises:
- a base portion anchored to a set location in a room; and
- a secondary portion comprising a quick-release feature for connection and disconnection from the base portion, wherein the secondary portion has one of the cords or poles attached thereto or is configured to receive attachment of one of the cords or poles.

23. The room divider of claim 21, wherein at least one of the one or more devices is nailed, screwed or adhered to a wall of a room.

24. The room divider of claim 21, wherein at least one of the one or more devices is nailed, screwed or adhered to a door of a room.

25. The room divider of claim 21, wherein at least one of the one or more devices is suctioned to a wall or door of a room.

26. The room divider of claim 21, wherein at least one of the one or more devices is a free-standing unit.

27. The room divider of claim 21, wherein the fastener is disposed at least 20 inches from an upper edge of the screen.

28. The room divider of claim 21, wherein the lower strut extends to an elevation at least 24 inches below the fastener.

* * * * *